United States Patent [19]

Chang et al.

[11] 4,395,554

[45] Jul. 26, 1983

[54] PROCESS FOR PRODUCING ALPHA-PICOLINE

[75] Inventors: Clarence D. Chang, Princeton; Patrick D. Perkins, Titusville, both of N.J.

[73] Assignee: Mobil Oil Corporation, New York, N.Y.

[21] Appl. No.: 369,296

[22] Filed: Apr. 16, 1982

Related U.S. Application Data

[63] Continuation-in-part of Ser. No. 326,258, Dec. 1, 1981, abandoned.

[51] Int. Cl.³ .......................................... C07D 213/16
[52] U.S. Cl. ................................. 546/250; 546/251
[58] Field of Search ............................... 546/250, 251

[56] References Cited

U.S. PATENT DOCUMENTS

| | | | |
|---|---|---|---|
| 3,272,865 | 9/1966 | Barker | 260/581 |
| 3,384,667 | 5/1968 | Hamilton | 260/585 |
| 3,860,650 | 1/1975 | Becker | 260/570 |
| 4,082,805 | 4/1978 | Kaeding | 260/585 |
| 4,220,783 | 9/1980 | Chang | 546/251 |

FOREIGN PATENT DOCUMENTS

| | | | |
|---|---|---|---|
| 2516316 | 10/1976 | Fed. Rep. of Germany | 564/402 |
| 49-29176 | 8/1974 | Japan | 564/402 |

OTHER PUBLICATIONS

Chem. Abs. XX, 39423(g), (1978).
Chang, Ser. No. 252,487, Filed 4/8/81.

*Primary Examiner*—Robert T. Bond
*Attorney, Agent, or Firm*—C. A. Huggett; M. G. Gilman; L. G. Wise

[57] ABSTRACT

Alpha-picolines are produced by containing aniline or substituted anilines, such as alkyl-, cyclo alkyl-, halo-; alkoxy- or substituted alkyl-anilines with a crystalline zeolite catalyst having a silica:alumina ratio of at least 12 and a constraint index of 1 to 12. ZSM-5 type catalysts are contacted at elevated temperature to yield alpha-picolines selectively.

13 Claims, No Drawings

PROCESS FOR PRODUCING ALPHA-PICOLINE

CROSS REFERENCE TO RELATED APPLICATIONS

This application is a continuation-in-part of our co-pending application Ser. No. 326,258, filed Dec. 1, 1981 and entitled Process for Producing Alpha-Picoline now abandoned.

FIELD OF THE INVENTION

This invention relates to a process for the production of alpha-picoline.

U.S. Patent Application Ser. No. 252,487, filed Apr. 8, 1981 by C. D. Chang and W. H. Lang discloses a process for converting phenol and phenolic-type compounds to aniline by reaction with ammonia or an amine over a zeolite catalyst of specified properties. The process produces aniline in good yields with high selectivity.

THE PRIOR ART

Alpha-picoline (2-methyl pyridine) is an important industrial material which is used as a solvent and as an intermediate in the production of various dyes and resins such as the ABS copolymers. It is currently made from acetaldehyde and ammonia with the beta and gamma picoline isomers and 2-methyl- 5-ethylpyridine being obtained as by-products.

Methods for producing nitrogenous aromatic compounds have been known in the past. For example, the Halcon-Scientific Design process has been used for the production of aniline by the gas phase ammonolysis of phenol at high pressure in the presence of a catalyst such as silica-alumina, with a promoter to inhibit coke formation. The process is described in "Industrial Organic Chemistry" Weissermel and Arpe, Verlag Chemie (Weinheim, N.Y.) 1978, pp. 327–330. In another process described in U.S. Pat. No. 3,860,650, organic amines are obtained by the ammoniation of phenolic compounds in the presence of a alumina catalyst. U.S. Pat. No. 3,272,865 describes a process for preparing aminated benzenes by reacting ammonia or another aminating agent with phenol or a substituted phenol at high temperature over an oxide catalyst.

U.S. Pat. No. 3,272,865 discloses a method for making aminated benzenes such as aniline from hydroxybenzenes such as phenol by reacting the phenol with ammonia over silica-alumina catalysts. The catalysts described in this patent are materials of low selectivity. A similar process is referred to in Chem. Abs. 88,39423 g.

U.S. Pat. No. 3,384,667 discloses a process for producing amines by the reaction of ammonia with an alcohol over a zeolite catalyst such as zeolites X or Y. These types of zeolites are, however, relatively nonselective catalysts which are subject to coking and rapid degeneration. U.S. Pat. No. 4,082,805 also discloses a process for producing amines by reacting ammonia with an alcohol over a zeolite catalyst but there is no suggestion that this process is capable of producing aromatic amines such as aniline or alpha picoline.

SUMMARY OF THE INVENTION

It has now been found that alpha-picoline and substituted alpha-picolines may be prepared by passing aniline or a substituted aniline over a zeolite catalyst. The product stream contains both aniline and alpha-picoline but the two may be readily separated by a number of different methods.

DESCRIPTION OF PREFERRED EMBODIMENTS

The starting material for the production of the alpha-picoline or the substituted alpha-picoline comprises an amminated benzene, that is, aniline or a substituted aniline. The substituents may be on the aromatic nucleus or on the amino group and there may be one or more of them. Typical nuclear substituents are alkyl groups such as methyl, ethyl, propyl (n- or iso-), butyl (n-, iso- or tert-), pentyl, hexyl, cycloalkyl groups such as cyclohexyl; alkoxy groups such as methoxy, ethoxy, propoxy or butoxy; halogen such as chloro, bromo, iodo or fluoro; substituted alkyl such as ethylamino, diethylamino and electronegative groups such as nitro, nitroso or hydroxy. Typical substituents on the amino group are alkyl groups such as methyl, ethyl, propyl or butyl. The substitutents may be of different types, e.g., as in 2-bromo-4-nitro aniline, 2,3-dimethyl-6-nitro aniline, 2-methoxy-3-nitro aniline and they may be on both the aromatic nucleus and the amino group as, for example, in N,N-dimethyl-3-bromo aniline; N,N-diethyl-2-ethoxy aniline; N,N-dimethyl-4-chloro-3- nitro aniline. A number of typical substituted anilines is disclosed in the Handbook of Chemistry and Physics, 61st Edition, R. C. Weast, Ed., CRC Press, to which reference is made. Although use of appropriately substituted anilines offers the possibility of producing substituted 2-methyl pyridines, we prefer to use aniline for the production of alpha-picoline (2-methyl pyridine) itself.

The starting material is passed over a zeolite catalyst to achieve the desired conversion. The zeolite catalysts used in the reaction comprise a three dimensional lattice of $SiO_4$ tetrahedra crosslinked by the sharing of oxygen atoms and which may optionally contain other atoms in the lattice, especially aluminum in the form of $AlO_4$ tetrahedra; the zeolite will also include a sufficient cationic complement to balance the negative charge on the lattice. Zeolites have a crystal structure which is capable of regulating the access to an egress from the intracrystalline free space. This control, which is effected by the crystal structure itself, is dependent both upon the molecular configuration of the material which is or, alternatively, is not, to have access to the internal structure of the zeolite and also upon the structure of the zeolite itself. The pores of the zeolite are in the form of rings which are formed by the regular disposition of the tetrahedra making up the anionic framework of the crystalline aluminosilicate, the oxygen atoms themselves being bonded to the silicon or aluminum atoms at the centers of the tetrahedra. A convenient measure of the extent to which a zeolite provides this control for molecules of varying sizes to its internal structure is provided by the Constraint Index of the zeolite: zeolites which provide but highly restricted access to and egress from the internal structure have a high value for the Constraint Index and zeolites of this kind usually have pores of small size. Contrariwise, zeolites which provide relatively free access to the internal zeolite structure have a low value for the Constraint Index. The method by which Constraint Index is determined is described fully in U.S. Pat. No. 4,016,218 to which reference is made for details of the method together with examples of Constraint Index for some typical zeolites. Because Constraint Index is related to the crystalline structure of the zeolite but is nevertheless determined by means of a test which exploits the capacity of the zeolite to engage in a cracking reaction, that is, a reaction dependent upon the possession of acidic sites and functionality in the zeolite, the sample of zeolite used in the test should be representative of zeolitic structure whose Constraint Index is to be determined and should also possess requisite acidic functionality for the test. Acidic functionality may, of course, be varied by artifices including base exchange, steaming or control of silica:alumina ratio.

A wide variety of acidic zeolites may be used in the present process including large pore zeolites such as faujasite, mordenite, zeolite X, zeolite Y and zeolite beta and small pore zeolites such as zeolite A but the most preferred group of zeolites are those which are characterized by a Constraint Index from 1 to 12 and a silica:alumina ratio of at least 12:1. The silica:alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica:alumina ratio is correctly determined.

Specific zeolites conforming to the prescribed values of Constraint Index and silica:alumina ratio include ZSM-5, ZSM-11, ZSM-12, ZSM-35 and ZSM-38 which are disclosed, respectively, in U.S. Pat. Nos. 3,702,886; 3,709,769; 3,832,449; 4,016,245 and 4,046,859. Reference is made to these patents for complete details of these zeolites and the preparation. Of them, ZSM-5 is preferred.

Zeolite beta is disclosed in U.S. Pat. No. 3,308,069 to which reference is made for details of this zeolite and its preparation.

When the zeolites have been prepared in the presence of organic cations they are catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; but it does appear to favor the formation of this special type of zeolite.

Some natural zeolites may sometimes be converted to zeolites of the desired type by various activation procedures and other treatments such as base exchange, steaming, alumina extraction and calcination.

The zeolites preferably have a crystal framework density, in the dry hydrogen form, not substantially below about 1.6 g.cm$^{-3}$. The dry density for known structures may be calculated from the number of silicon plus aluminum atoms per 1000 cubic Angstroms, as given, e.g., on page 19 of the article on Zeolite Structure by W. M. Meier included in "Proceedings of the Conference on Molecular Sieves, London, April 1967", published by the Society of Chemical Industry, London, 1968. Reference is made to this paper for a discussion of the crystal framework density. A further discussion of crystal framework density, together with values for some typical zeolites, is given in U.S. Pat. No. 4,016,218, to which reference is made.

When synthesized in the alkali metal form, the zeolite is conveniently converted to the hydrogen form, generally by intermediate formation of the ammonium form as a result of ammonium ion exchange and calcination of the ammonium form to yield the hydrogen form. It has been found that although the hydrogen form of the zeolite catalyzes the reaction successfully, the zeolite may also be partly in the alkali metal form although the selectivity to alpha-picoline is lower with the zeolite in this form.

It may be desirable to incorporate the zeolite in another material resistant to the temperature and other conditions employed in the process. Such matrix materials include synthetic or naturally occurring or in the form of gelatinous precipitates or gels including mixtures of silica and metal oxides. Naturally occurring clays can be composited with the zeolite and they may be used in the raw state as originally mined or initially subjected to calcination, acid treatment or chemical modification. Alternatively, the zeolite may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia or silica-magnesia-zirconia. The matrix may be in the form of a cogel. The relative proportions of zeolite component and inorganic oxide gel matrix may vary widely with the zeolite content typically ranging from 1 to 99 percent by weight and more usually in the range of 5 to 80 percent weight of the composite.

The process is highly selective for the production of alpha picoline. Only minor amounts of by-products such as toluidines, diphenylamines and heterocyclics are obtained. Aniline conversions and selectivity to the production of alpha-picoline are both favored by higher temperatures and by the presence of ammonia. The ratio of ammonia to aniline in the feed is suitably from 0.5:1 to 25:1 molar and will usually be from 1:1 to 20:1 molar.

The starting material is passed over the catalyst at an elevated temperature, normally in the range of 200° C. to 650° C. (about 400° F. to 1200° F.), preferably from 400° C. to 550° C. (about 750° F. to 1020° F.) and at such temperatures the aniline starting material will normally be in the vapor phase. Superatmospheric pressures are normally employed but the pressure may range from atmospheric to much higher values, the maximum normally being dictated by practical considerations. Pressures from atmospheric up to 25,000 kPa (about 3,600 psig) are suitable, preverably from 2,500 to 5,000 kPa (about 350 to 710 psig), although if a low pressure is to be employed, it should be sufficient to provide the desired flow rate and space velocity and for this purpose a pressure of 200 kPa (about 15 psig) will normally be required. Space velocity is normally in the range 0.1 to 50 WHSV, preferably 0.2 to 5 WHSV. An inert carrier gas such as nitrogen or helium may be used at a higher space velocity e.g. 50 to 500 GHSV.

The use of higher temperatures will, in general lead to increased aniline conversion but excessively high temperatures, for instance, over 650° C., should normally be avoided because they result in poor selectivity to the production of alpha-picoline. The degree of conversion is favored by the use of higher pressures and selectivity to alpha-picoline by the presence of ammonia in high ratios relative to aniline. The use of the higher ammonia:aniline ratios also tends to suppress the formation of diphenylamine and other by-products of the reaction.

The conversion of the aniline to the alpha-picoline is acid catalyzed and because of this, the zeolite should be at least partly in the hydrogen or acidic form. The acidity of the zeolite may conveniently be measured by its alpha value which is a measure of the relative activity of the zeolite with respect to a high activity silica:alumina cracking catalyst. A method for the determination of alpha is given in U.S. Pat. No. 4,016,218 and the Journal of Catalysis, Vol. VI, pages 278-287, 1966, to which reference is made for details of the method. The alpha value of the zeolite used in the present process will usually be at least 1 and, as a general rule, at least 10. The alpha values of the preferred HZSM-5 zeolites having a silica:alumina ratio of 70:1 are normally in the range of 10 to 50. Higher alpha catalysts may however be used. Alpha values may be varied by a number of known techniques such as steaming or sodium exchange, both of which reduce alpha. Alpha may be increased almost up to the theoretical limit set by the acid site density of the zeolite by ammonium exchange followed by calcination. The acidity of the zeolite may also be varied by control of the silica:alumina ratio of the zeolite, as described in U.S. Pat. No. 4,218,573, to which reference is made.

The alpha-picoline may be separated from the product stream by a number of different physical or chemical methods. Distillation is a convenient and preferred method as the boiling point of alpha-picoline is 129.4° C. and that of aniline, the starting material is 184.4° C. Extraction techniques may also be employed, using solvents having different affinities for the different components of the product stream; water is a suitable solvent for this purpose as alpha-picoline is infinitely soluble in it whereas aniline has a solubility of only 3.6% at 18° C. Successive extractions may be used to obtain a product of requisite purity. Appropriate separation techniques may also be performed after the components of the product stream have been converted to derivatives; when separation has been completed the derivative may be converted back to the original material. Unreacted starting material may be recycled after separation of products in order to obtain a satisfactory total conversion.

Because the higher temperatures provide a greater degree of conversion, the reaction will normally be carried out in the vapor phase, usually in the presence of ammonia and an inert carrier gas such as nitrogen. Liquid phase reactions are not, however, excluded and they may use solvents or other diluents such as benzene.

The process is notable for the high selectivity to the production of the alpha isomer of picoline; the beta and gamma isomers are completely absent and other by-products may be produced in only minor amounts. The present process therefore provides a highly attractive synthetic procedure.

The invention is illustrated by the following Examples.

EXAMPLES 1-6

Aniline was converted to alpha-picoline by passing aniline and ammonia over an HZSM-5 catalyst at elevated temperature and pressure, using nitrogen as a carrier gas. The catalyst was used either in the form (Example 1) or composited with 35 weight percent $Al_2O_3$ binder and steamed after compositing (Examples 2-6). The conditions employed, together with the analyses of the product streams are given in Table 1 below.

TABLE 1

| | Example No. | | | | | |
|---|---|---|---|---|---|---|
| Catalyst | 1 HZSM-5 pure | 2 | 3 | 4 | 5 | 6 |
| | | 35% $Al_2O_3$ binder, steamed | | | | |
| Alpha value | 192 | 340 | 340 | 340 | 340 | 340 |
| Temp., °C. | 510 | 510 | 510 | 510 | 510 | 540 |
| Pressure, kPa | 2860 | 2860 | 2860 | 2860 | 5620 | 5620 |
| WHSV ammonia (binder free) | 1.66 | 1.00 | 0.30 | 2.80 | 2.80 | 2.80 |
| WHSV aniline (binder free) | 1.11 | 0.90 | 0.90 | 0.90 | 0.90 | 0.90 |
| Ammonia/aniline ratio, mol wt. | 1.50 | 1.10 | 0.30 | 3.10 | 3.10 | 3.10 |
| GHSV $N_2$ | 100 | 100 | 100 | 100 | 100 | 100 |
| Conversion of aniline, % | 13.10 | 11.60 | 8.30 | 11.70 | 17.90 | 27.70 |
| Product selectivity, Wt. % | | | | | | |
| Alpha-Picoline | 51.60 | 46.80 | 32.60 | 54.00 | 56.60 | 32.60 |
| Toluidines | 16.10 | 21.30 | 17.60 | 22.30 | 22.30 | 21.30 |
| Xylidines | 2.70 | 7.40 | 8.90 | 6.50 | 7.20 | 5.30 |
| Diphenylamine | t | 17.80 | 29.40 | 3.80 | 1.00 | 0.60 |
| Indole | 4.60 | — | — | 1.30 | — | — |
| Methylindoles | 0.50 | — | — | — | — | — |
| Quinoline | 6.10 | — | — | 4.20 | 4.80 | 4.50 |
| Methylquinolines | 2.50 | — | — | 0.20 | 0.40 | 4.00 |
| Carbazole | 0.70 | — | — | — | — | — |
| Acridine | t | 5.70 | 5.30 | 1.40 | — | 0.80 |
| Pyridine | — | — | — | 2.40 | 2.30 | 4.30 |
| Lutidines | 0.60 | — | — | 3.30 | 4.00 | 4.80 |
| Acetonitrile | 4.00 | — | — | — | — | 5.40 |
| Propionitrile | — | — | — | — | — | 5.60 |
| Benzonitrile | 0.38 | 1.00 | 6.20 | 0.60 | 1.40 | 8.20 |
| Benzene | 3.80 | — | — | — | — | 0.60 |

TABLE 1-continued

| | Example No. | | | | | |
|---|---|---|---|---|---|---|
| | 1 | 2 | 3 | 4 | 5 | 6 |
| Catalyst | HZSM-5 pure | | 35% Al$_2$O$_3$ binder, steamed | | | |
| Toluene | 2.90 | — | — | — | — | 2.00 |

EXAMPLE 7

Aniline was passed over HZSM-5 (silica:alumina 70:1) at 540° C., 2860 kPa in the absence of ammonia using nitrogen gas as a carrier (0.37 WHSV aniline, 100 GHSV nitrogen). The overall conversion was 7.1 percent to the products shown in Table 2 below.

TABLE 2

| Reaction Product Distribution, Wt. Percent | |
|---|---|
| Alpha picoline | 9.6 |
| Toluidines | 18.6 |
| Xylidines | 2.8 |
| Diphenylamine | 49.1 |
| Indole | 6.0 |
| Methylindole | 0.4 |
| Quinoline | 1.5 |
| Methylquinoline | 0.3 |
| Carbazole | Trace |
| Acridine | Trace |
| Benzonitrile | 8.4 |
| Benzene | 2.0 |
| Toluene | 1.3 |

EXAMPLE 8

Aniline was passed over a zeolite beta catalyst at a temperature of 510° C., 2860 kPa, in the presence of ammonia using nitrogen gas as a carrier (1.11 WHSV aniline, 1.66 WHSV ammonia, 100 GHSV nitrogen). The aniline conversion was 2 percent with a 45 percent selectivity to alpha-picoline. Other products included diphenylamine (3 percent selectivity), carbazole (46 percent selectivity) and isomeric toluidines (6 percent selectivity).

We claim:

1. A method of making alpha-picoline or a substituted alpha picoline by contacting aniline or a substituted aniline with a crystalline zeolite catalyst.

2. A method according to claim 1 in which aniline is contacted with the zeolite to form alpha-picoline.

3. A method according to claim 2 in which the aniline is contacted with the zeolite in the presence of ammonia.

4. A method according to claim 3 in which the molar ratio of the ammonia to the aniline is from 0.5:1 to 25:1.

5. A method according to claim 1 in which the zeolite has a silica:alumina ratio of at least 12:1 and a Constraint Index of 1 to 12.

6. A method according to claim 5 in which the zeolite is ZSM-5.

7. A method according to claim 5 in which the zeolite is ZSM-11.

8. A method according to claim 5 in which the zeolite is ZSM-12.

9. A method according to claim 5 in which the zeolite is ZSM-35.

10. A method according to claim 5 in which the zeolite is ZSM-38.

11. A method according to claim 2 in which the aniline is contacted with the zeolite at a temperature from 200° C. to 650° C., a pressure from 200 to 25,000 kPa and a space velocity of 0.1 to 50 WHSV.

12. A method of making alpha-picolines by contacting aniline or a substituted aniline with a crystalline zeolite catalyst, said substituted aniline being substituted in the aromatic nucleus or amino group with one or more alkyl, cycloalkyl, alkoxy, halogen, nitro or substituted-alkyl group.

13. A catalytic process for converting aniline to alpha-picoline in the presence of ammonia which comprises the steps of contacting a vapor phase reaction mixture of ammonia and aniline having a molar ratio of about 0.5:1 to 25:1 ammonia to aniline with a ZSM-5 type crystalline aluminosilicate catalyst at a temperature of about 200° C. to 650° C. and a space velocity of about 0.1 to 50 WHSV.

* * * * *